(12) United States Patent
Sun et al.

(10) Patent No.: US 9,320,769 B2
(45) Date of Patent: Apr. 26, 2016

(54) PHARMACEUTICAL COMPOSITION FOR RELIEVING FATIGUE AND PREPARATION METHOD THEREOF

(75) Inventors: Dejun Sun, Jilin (CN); Jinlong Yin, Jilin (CN); Miaonan Sun, Jilin (CN); Yizhuo Zhao, Jilin (CN); Chunsheng Guo, Jilin (CN); Xue Li, Jilin (CN); Yanhui Gao, Jilin (CN)

(73) Assignee: Jilin Zixin Pharmaceutical Research Institution LLC., Changchun, Jilin (CN)

( * ) Notice: Subject to any disclaimer, the term of this patent is extended or adjusted under 35 U.S.C. 154(b) by 357 days.

(21) Appl. No.: 13/980,554

(22) PCT Filed: Jul. 15, 2011

(86) PCT No.: PCT/CN2011/077174
§ 371 (c)(1),
(2), (4) Date: Jul. 18, 2013

(87) PCT Pub. No.: WO2012/097577
PCT Pub. Date: Jul. 26, 2012

(65) Prior Publication Data
US 2013/0302310 A1 Nov. 14, 2013

(30) Foreign Application Priority Data
Jan. 21, 2011 (CN) .......................... 2011 1 0023456

(51) Int. Cl.
| | | |
|---|---|---|
| *A61K 36/00* | (2006.01) |
| *A61K 36/25* | (2006.01) |
| *A61K 36/481* | (2006.01) |
| *A61K 36/296* | (2006.01) |
| *A61K 36/894* | (2006.01) |
| *A61K 36/8969* | (2006.01) |
| *A61K 36/43* | (2006.01) |
| *A61K 36/815* | (2006.01) |
| *A61K 36/35* | (2006.01) |
| *A61K 36/258* | (2006.01) |
| *A61K 36/39* | (2006.01) |
| *A61K 36/8945* | (2006.01) |
| *A61K 35/74* | (2015.01) |
| *A61K 36/88* | (2006.01) |

(52) U.S. Cl.
CPC ................ *A61K 36/35* (2013.01); *A61K 35/74* (2013.01); *A61K 36/258* (2013.01); *A61K 36/296* (2013.01); *A61K 36/39* (2013.01); *A61K 36/43* (2013.01); *A61K 36/481* (2013.01); *A61K 36/815* (2013.01); *A61K 36/88* (2013.01); *A61K 36/8945* (2013.01); *A61K 36/8969* (2013.01)

(58) Field of Classification Search
None
See application file for complete search history.

(56) References Cited

FOREIGN PATENT DOCUMENTS

| | | |
|---|---|---|
| CN | 1144128 | 3/1997 |
| CN | 1227261 | 9/1999 |
| CN | 101181351 | 5/2008 |
| CN | 102078512 | 6/2011 |

*Primary Examiner* — Qiuwen Mi

(57) ABSTRACT

A pharmaceutical composition for relieving fatigue and preparation method thereof are provided. The pharmaceutical composition is prepared by mixing ethanol extract of ginseng, ethanol extract of *astragalus*, ethanol extract of *epimedium*, ethanol extract of yam, ethanol extract of *polygonatum*, ethanol extract of dodder, aqueous extract of wolfberry and a fermentation conversion solution of fruits and vegetables.

18 Claims, No Drawings

PHARMACEUTICAL COMPOSITION FOR RELIEVING FATIGUE AND PREPARATION METHOD THEREOF

CROSS REFERENCE OF RELATED APPLICATION

This is a U.S. National Stage under 35 U.S.C. 371 of the International Application PCT/CN2011/077174, filed Sep. 15, 2011, which claims priority under 35 U.S.C. 119(a-d) to CN 201110023456.6, filed Jan. 21, 2011.

BACKGROUND OF THE PRESENT INVENTION

1. Field of Invention

The present invention relates to a pharmaceutical composition for relieving fatigue and a preparation method thereof.

2. Description of Related Arts

Fatigue is a signal that reminds the body that loads are more than normal and adjustments and rests are needed. If the fatigue has been a long-term state, not only work efficiency will be reduced, but also diseases are induced. Some people have tiredness, listlessness, yawns, restlessness, irritability, backache, back pain, dizziness, vertigo, insomnia, drowsiness, weakness, malaise, trance, loss of appetite, chronic fatigue too often but no clear reason is found; although medicines for brain nerves, respiratory tracts and other purposes are taken, general malaise symptoms are still not improved. This is the typical fatigue, and attention should be attracted.

Ginseng: a root of *panax* of the family Araliaceae. More than 30 kinds of ginseng saponins and polysaccharides can be separated out from the ginseng.

Yam: also known as *dioscorea opposita*, belonging to the genus *Dioscorea* of the family Dioscoreaceae. The yam complements rather than stagnates, and doesn't cause dryness-heat, the yam is good to spleen and stomach, and is only used as an auxiliary for lungs and kidney. The yam is often used in many anti-aging prescriptions. Vitro experiments of aqueous extract of the yam have showed that the yam is capable of promoting interferon production and increasing a number of T cells. In the study of rats with experimental arthritis, the aqueous extract of the yam significantly inhibits denaturation of gamma globulin caused by $Cu^{2+}$, and anti-arthritis function of the yam is indicated. The aqueous extract of the yam can also eliminate urine protein, suppress generation of mutant cells.

Wolfberry: a dried ripe fruit of *lycium barabrum* of the family Solanaceae. The wolfberry Contains betaine, amino acid, carotene, vitamin B1, B2 and C, calcium, phosphorus, iron as well as other ingredients. Pharmacological studies have confirmed that the wolfberry can regulate immunity, effectively inhibit growth of tumor and cell mutation, the wolfberry has functions such as anti-aging, anti-fatty liver, regulating blood fat as well as blood sugar and promoting hematopoietic ability, and thus the wolfberry adapts to clinical application. The wolfberry is easy to take and can be added in the medicine, chewed or infused in wine. However, the wolfberry should not be taken during cold, fever, poor spleen and diarrhea.

*Astragalus*: also known as milk-vetch, a name for plants of the genus *Astragalus* as well as herbal medicines made by the plants. Chemical composition: flavonoids calycosin, 3-hydroxy-9,10-dimethoxy pterocarpan as well as astragaloside I, V and III. The *astragalus* promotes immunity, arrests sweating, protects viscus from prolapse, eliminates toxicant, promotes tissue regeneration, induces diuresis and removes edema. The *astragalus* cures weakness, viscus prolapse, chronic diarrhea, rectal prolapse, hematochezia, uterine bleeding, poor immunity, spontaneous perspiration, chronic edema, chronic ulcer, blood deficiency, chlorosis, influenza, frequent urination, chronic nephritis, proteinuria, diabetes, etc. The cooked *astragalus* promotes immunity, the raw *astragalus* eliminates toxicant.

*Epimedium*: a dried aboveground part of *Epimedium parvifolium, Epimedium brevicornum* Maxim, *Epimedium Sagittaturn* (Sieb. et Zucc.) Maxim, *Epimedium pubescens* Maxim, *Epimedium wushanense* T. S. Ying or *Epimedium koreanum* Nakai of the genus *Epimedium* of the family Berberidaceae. The *epimedium* cures rheumatism, arthritis, and limb numbness or cramp, Clematis, the *epimedium* is often used with Chinese clematis, morinda officinalis, cinnamon, angelica and ligusticum wallichii.

*Polygonatum*: also known as Solomon's seal, a dried root of *kingianum* Coll. et Hemsl, *Polygonatum sibiricum* Red or *Polygonatum cyrtonema* Hua. The root of the *polygonatum* can be taken as the medicine. The *polygonatum* does good to the immunity, the spleen, the lung, and the kidney. The *polygonatum* cures cough; pneumonia; spleen weakness; anorexia; thirsty; diabetes; renal deficiency; impotence, nocturnal emission; tinnitus, dim eyesight; premature graying; physical weakness win; and scabies or ringworm. Particularly, the *polygonatum* is very effective for the diabetes.

Dodder: a seed of the *Cuscuta chinessis* Lam of the Convolvulaceae, containing resin-like glycosides, cholesterol, campesterol, sitosterol, stigmasterol and triterpene acids, sugars. The dodder is sweet and bland. The dodder nourishes the liver and the kidney, reduces urination, prevents abortion, improves eyesight and stops the diarrhea. The dodder cures impotence, nocturnal emission, enuresis, frequent urination, weak waist and knee, tinnitus, dim eyesight, kidney weakness, fetal irritability, spleen and kidney deficiency and the diarrhea; and cures vitiligo if uses externally.

SUMMARY OF THE PRESENT INVENTION

An object of the present invention is to provide a pharmaceutical composition for relieving fatigue and a preparation method thereof.

Accordingly, in order to accomplish the above object, the present invention provides a preparation method of a pharmaceutical composition for relieving fatigue, comprising:

mixing the following eight substances for obtaining a mixture, wherein the mixture is the pharmaceutical composition for relieving the fatigue:

A. ethanol extract of ginseng; B. ethanol extract of *astragalus*; C. ethanol extract of *epimedium*; D. ethanol extract of yam; E. ethanol extract of *polygonatum*; F. ethanol extract of dodder; G. aqueous extract of wolfberry; H. a fermentation conversion solution of fruits and vegetables;

wherein a method for preparing the A substance comprises: processing reflux extraction on the ginseng with an aqueous solution of ethanol for obtaining extract, wherein the extract is the ethanol extract of ginseng;

wherein a method for preparing the B substance comprises: processing the reflux extraction on the *astragalus* with the aqueous solution of the ethanol for obtaining the extract, wherein the extract is the ethanol extract of *astragalus*;

wherein a method for preparing the C substance comprises: processing the reflux extraction on the *epimedium* with the aqueous solution of the ethanol for obtaining the extract, wherein the extract is the ethanol extract of *epimedium*;

wherein a method for preparing the D substance comprises: processing the reflux extraction on the yam with the aqueous solution of the ethanol for obtaining the extract, wherein the extract is the ethanol extract of yam;

wherein a method for preparing the E substance comprises: processing the reflux extraction on the *polygonatum* with the aqueous solution of the ethanol for obtaining the extract, wherein the extract is the ethanol extract of *polygonatum*;

wherein a method for preparing the F substance comprises: processing the reflux extraction on the dodder with the aqueous solution of the ethanol for obtaining the extract, wherein the extract is the ethanol extract of dodder;

wherein a method for preparing the G substance comprises: processing heating extraction on the wolfberry with pure water for obtaining the extract, wherein the extract is the aqueous extract of wolfberry;

wherein a method for preparing the H substance comprises steps of: mixing the fruits and the vegetables, a bacteria liquid of *Lactobacillus acidophilus*, the bacteria liquid of the *Bifidobactreium longum*, the bacteria liquid of the *Lactobacillus delbrueckii* subsp *bulgaricus* and the bacteria liquid of the *Streptococcus thermophilus*, fermenting for obtaining a fermentation product, wherein the fermentation product is the fermentation conversion solution of fruits and vegetables.

A mass ratio of the ginseng, the wolfberry, the yam, the astragalus, the epimedium, the polygonatum and the dodder is (1.2~1.8):(2.5~3.5):(2.5~3.5):(2.5~3.5):(0.5~1.5):(2.5~3.5):(2.5~3.5); preferably, the mass ratio of the ginseng, the wolfberry, the yam, the *astragalus*, the *epimedium*, the *polygonatum* and the dodder is (1.2, 1.4 or 1.8):(2.5, 3.0 or 3.5):(2.5, 3.0 or 3.5):(2.5, 3.0 or 3.5):(0.5, 1.0 or 1.5):(2.5, 3.0 or 3.5):(2.5, 3.0 or 3.5).

Preferably, in the methods for preparing the A, B, C, D, E and F substances:

reflux extraction time is 2 h~5 h, the reflux extraction time is preferably 2 h, 3 h or 5 h;

concentration of the aqueous solution of ethanol is 70% (according to volume fraction);

wherein in the method for preparing the G substance:

heating extraction time is 2 h~5 h, heating extraction temperature is 70° C.~90° C.; the heating extraction time is preferably 2 h, 3 h or 5 h, the heating extraction temperature is preferably 70° C., 80° C., or 90° C.;

wherein in the method for preparing the H substance:

fermentation temperature is 18° C.~37° C., the fermentation temperature is preferably 18° C., 23° C. or 37° C., fermentation time is 10 days to 180 days, the fermentation time is preferably 10 days, 15 days or 180 days, a fermentation method is stirring while fermenting.

The method for preparing the A substance further comprises steps of:

removing the ethanol from the extract, and then concentrating and drying for obtaining a dried product, wherein the dried product is the ethanol extract of the ginseng;

the method for preparing the B substance further comprises steps of:

removing the ethanol from the extract, and then concentrating and drying for obtaining the dried product, wherein the dried product is the ethanol extract of the *astragalus*;

the method for preparing the C substance further comprises steps of:

removing the ethanol from the extract, and then concentrating and drying for obtaining the dried product, wherein the dried product is the ethanol extract of the *epimedium*;

the method for preparing the D substance further comprises steps of:

removing the ethanol from the extract, and then concentrating and drying for obtaining the dried product, wherein the dried product is the ethanol extract of the yam;

the method for preparing the E substance further comprises steps of:

removing the ethanol from the extract, and then concentrating and drying for obtaining the dried product, wherein the dried product is the ethanol extract of the *polygonatum*;

the method for preparing the F substance further comprises steps of:

removing the ethanol from the extract, and then concentrating and drying for obtaining the dried product, wherein the dried product is the ethanol extract of the dodder;

the method for preparing the G substance further comprises: concentrating and drying the extract for obtaining the dried product, wherein the dried product is the aqueous extract of the wolfberry;

the method for preparing the H substance further comprises a step of:

crushing the fruits and vegetables into 40~50 meshes size before the fermentation;

after the fermentation, the method for preparing the H substance further comprises steps of: filtering the fermentation product, collecting filtrate, ultrafiltering, collecting ultrafiltrate, wherein the ultrafiltrate is the fermentation conversion solution of fruits and vegetables.

Preferably, ultrafiltration is filtering the filtrate with 100,000 molecular weight ultrafiltration membrane (an inputting pressure is 1.3 kg, an outputting pressure is 0.5 kg).

The fruits and vegetables are the mixture of the following 54 kinds of fruits and vegetables:

konjac, eggplant, asparagus, spinach, bean sprout, broccoli, cabbage, turnip, cucumber, pea, red pepper, celery, scallion, garlic, grape, grapefruit, watermelon, peach, orange, blueberry, orange, banana, lychee, bitter gourd, leek, pomegranate, dragon fruit, carrot, tomato, Chinese cabbage, celery, bell pepper, lettuce, pear, ginger, taro, bean, pumpkin, lotus root, cherry, kiwi, plum, strawberry, fig, kumquat, citrus, Southland pear, melon, cantaloupe, pawpaw, onion, mulberry, sugar beet and lemon.

Preferably, each fruit or vegetable is of the same weight.

In the method for preparing the pharmaceutical composition for relieving fatigue, 1 L the mixture is prepared by: mixing (5~50) g the ethanol extract of the ginseng, (5~100) g the ethanol extract of the *astragalus*, (5~50) g the ethanol extract of the *epimedium*, (5~50) g the ethanol extract of the yam, (5~50) g the ethanol extract of the *polygonatum*, (5~50) g the ethanol extract of the dodder, (5~100) g the aqueous extract of the wolfberry and the fermentation conversion solution of the fruits and vegetables, adding the fermentation conversion solution of fruits and vegetables for making up a volume to 1 L;

preferably, 1 L the mixture is prepared by: mixing (5, 25 or 50) g the ethanol extract of the ginseng, (5, 50 or 100) g the ethanol extract of the *astragalus*, (5, 20 or 50) g the ethanol extract of the *epimedium*, (5, 20 or 50) g the ethanol extract of the yam, (5, 30 or 50) g the ethanol extract of the *polygonatum*, (5, 20 or 50) g the ethanol extract of the dodder, (5, 50 or 100) g the aqueous extract of the wolfberry and the fermentation conversion solution of the fruits and vegetables, adding the fermentation conversion solution of fruits and vegetables for making up a volume to 1 L;

in the method for preparing the A substance:

a ratio of the aqueous solution of the ethanol and the ginseng is (1~10) ml:1 g;

preferably, the ratio of the aqueous solution of the ethanol and the ginseng is (1, 5 or 10) ml:1 g;

in the method for preparing the B substance:
the ratio of the aqueous solution of the ethanol and the *astragalus* is (1~10) ml:1 g;
preferably, the ratio of the aqueous solution of the ethanol and the *astragalus* is (1, 6 or 10) ml:1 g;
in the method for preparing the C substance:
the ratio of the aqueous solution of the ethanol and the *epimedium* is (1~10) ml:1 g;
preferably, the ratio of the aqueous solution of the ethanol and the *epimedium* is (1, 8 or 10) ml:1 g;
in the method for preparing the D substance:
the ratio of the aqueous solution of the ethanol and the yam is (1~10) ml:1 g;
preferably, the ratio of the aqueous solution of the ethanol and the yam is (1, 8 or 10) ml:1 g;
in the method for preparing the E substance:
the ratio of the aqueous solution of the ethanol and the *polygonatum* is (1~10) ml:1 g;
preferably, the ratio of the aqueous solution of the ethanol and the *polygonatum* is (1, 8 or 10) ml:1 g;
in the method for preparing the F substance:
the ratio of the aqueous solution of the ethanol and the dodder is (1~10) ml:1 g;
preferably, the ratio of the aqueous solution of the ethanol and the dodder is (1, 8 or 10) ml:1 g;
in the method for preparing the G substance:
the ratio of the pure water and the wolfberry is (1~150) ml:1 g;
preferably, the ratio of the pure water of the ethanol and the wolfberry is (1, 30 or 150) ml:1 g;
in the method for preparing the H substance:
the ratio of the bacteria liquid of the *Lactobacillus acidophilus*, the bacteria liquid of the *Bifidobactreium longum*, the bacteria liquid of the *Lactobacillus delbrueckii* subsp *bulgaricus*, the bacteria liquid of the *Streptococcus thermophilus*, the fermentation conversion solution of the fruits and vegetables and water is (2000~8000) ml:(2000~8000) ml:(2000~8000) ml:(2000~8000) ml:(1000~1500) kg:(1000~1500) kg;
preferably, the ratio of the bacteria liquid of the *Lactobacillus acidophilus*, the bacteria liquid of the *Bifidobactreium longum*, the bacteria liquid of the *Lactobacillus delbrueckii* subsp *bulgaricus*, the bacteria liquid of the *Streptococcus thermophilus*, the fermentation conversion solution of the fruits and vegetables and the water is (2000, 5000 or 8000) ml:(2000, 5000 or 8000) ml:(2000, 5000 or 8000) ml:(2000, 5000 or 8000) ml:(1000, 1200 or 1500) kg:(1000, 1200 or 1500) kg.

A method for preparing the bacteria liquid of the *Lactobacillus acidophilus* comprises: fermenting and growing *Lactobacillus acidophilus* for obtaining the fermentation production, wherein the fermentation production is the bacteria liquid of the *Lactobacillus acidophilus*; wherein the fermentation temperature is 20° C.~41° C., the fermentation temperature is preferably 20° C., 37° C. or 41° C., the fermentation time is 15 h~36 h, the fermentation time is preferably 15 h, 16 h or 36 h;

a method for preparing the bacteria liquid of the *Bifidobactreium longum* comprises: fermenting and growing *Bifidobactreium longum* for obtaining the fermentation production, wherein the fermentation production is the bacteria liquid of the *Bifidobactreium longum*; wherein the fermentation temperature is 20° C.~41° C., the fermentation temperature is preferably 20° C., 37° C. or 41° C., the fermentation time is 15 h~36 h, the fermentation time is preferably 15 h, 16 h or 36 h;

a method for preparing the bacteria liquid of the *Lactobacillus delbrueckii* subsp *bulgaricus* comprises: fermenting and growing *Lactobacillus delbrueckii* subsp *bulgaricus* for obtaining the fermentation production, wherein the fermentation production is the bacteria liquid of the *Lactobacillus delbrueckii* subsp *bulgaricus*; wherein the fermentation temperature is 20° C.~41° C., the fermentation temperature is preferably 20° C., 37° C. or 41° C., the fermentation time is 15 h~36 h, the fermentation time is preferably 15 h, 16 h or 36 h;

a method for preparing the bacteria liquid of the *Streptococcus thermophilus* comprises: fermenting and growing *Streptococcus thermophilus* for obtaining the fermentation production, wherein the fermentation production is the bacteria liquid of the *Streptococcus thermophilus*; wherein the fermentation temperature is 20° C.~41° C., the fermentation temperature is preferably 20° C., 37° C. or 41° C., the fermentation time is 15 h~36 h, the fermentation time is preferably 15 h, 16 h or 36 h.

The *Lactobacillus acidophilus* is the *Lactobacillus acidophilus* CGMCC (China General Microbiological Culture Collection) 1.1854, the *Bifidobactreium longum* is the *Bifidobactreium longum* CGMCC 1.2186, the *Lactobacillus delbrueckii* subsp *bulgaricus* is the *Lactobacillus delbrueckii* subsp *bulgaricus* CGMCC 1.1480, the *Streptococcus thermophilus* is the *Streptococcus thermophilus* CGMCC 1.2471.

A growth medium prescription for fermental cultivation: mixing 10 g peptone, 10 g beef extract, 5 g yeast extract, 20 g glucose, 1 g Tween-80, 2 g $K_2HPO_4$, 1 g Tween-80, 5 g NaAC, 2 g triammonium citrate, 0.2 g $MgSO_4$, 0.05 g $MnSO_4$ and the water, making up to 1 L by the water for obtaining the growth medium. The pharmaceutical composition prepared by the above methods for improving the fatigue is also within protection scope of the present invention.

The pharmaceutical composition for relieving the fatigue prepared by the method is within the scope of the present invention.

Experiments of the present invention illustrates that extracting time for obtaining the ethanol extract of the ginseng, the ethanol extract of the *astragalus*, the ethanol extract of the *epimedium*, the ethanol extract of the yam, the ethanol extract of the *polygonatum*, the ethanol extract of the dodder, the aqueous extract of the wolfberry and the fermentation conversion solution of the fruits and vegetables is short, the above main ingredients can be used for preparing the pharmaceutical composition for relieving the fatigue, and because a larger proportion of the Chinese with weak immunity are in a sub-health state and may be accompanied by hyperglycemia at the same time, the present invention utilizes compound sweetener as a flavoring agent in oral liquid for reducing the glucose, sucrose and other sweeteners which can easily cause the hyperglycemia in such a manner that more people are benefited.

These and other objectives, features, and advantages of the present invention will become apparent from the following detailed description, the accompanying drawings, and the appended claims.

DETAILED DESCRIPTION OF THE PREFERRED EMBODIMENT

Experimental methods used in the following preferred embodiments are conventional methods except for special instructions.

Ingredients and agents used in the following preferred embodiments are commercially available except for special instructions.

Preferred Embodiment 1

Obtaining Ferment Composition of Ginseng for Relieving Fatigue

Method I:

wherein the active ingredients of the ferment composition of the ginseng are: 1.4 g the ginseng, 3.0 g wolfberry, 3.0 g yam, 3.0 g *astragalus,* 1.0 g *epimedium,* 3.0 g *polygonatum* and 3.0 g dodder;

a) preparing ethanol extract of the ginseng:

1. preparing the ingredient: wherein the ginseng purchased from Jilin Zixin Pharmaceutical Industrial Co., Ltd is in line with the Pharmacopoeia of the People's Republic of China; quality is strictly controlled before feeding according to corporate standards;

2. weighting the ginseng according to a prescription, washing with water and drying the ginseng, processing reflux extraction twice with a 10-flod (v/w) 70% aqueous solution of ethanol, reflux extraction time for once is 3 h, filtrating extract, combining filtrate, vacuum recovering the ethanol;

3. concentrating the filtrate to a relative density of 1.10~1.15 (0.07 MPa, 70° C.), spray-drying the filtrate (inputting temperature is 170° C., outputting temperature is 70° C.) for obtaining spray-dried powder, wherein the powder is the ethanol extract of the ginseng;

b) preparing ethanol extract of the *astragalus:*

1. preparing the ingredient: wherein the *astragalus* purchased from Jilin Zixin Pharmaceutical Industrial Co., Ltd is in line with the Pharmacopoeia of the People's Republic of China; the quality is strictly controlled before feeding according to the corporate standards;

2. weighting the *astragalus* according to the prescription, washing with the water and drying the *astragalus*, processing the reflux extraction three times with the 6-flod (v/w) 70% aqueous solution of the ethanol, the reflux extraction time for once is 3 h, filtrating the extract, combining the filtrate, vacuum recovering the ethanol;

3. concentrating the filtrate to the relative density of 1.10~1.15 (0.07 MPa, 70° C.), spray-drying the filtrate (the inputting temperature is 170° C., the outputting temperature is 70° C.) for obtaining the spray-dried powder, wherein the powder is the ethanol extract of the *astragalus;* c) preparing ethanol extract of the *epimedium:*

1. preparing the ingredient: wherein the *epimedium* purchased from Jilin Zixin Pharmaceutical Industrial Co., Ltd is in line with the Pharmacopoeia of the People's Republic of China; the quality is strictly controlled before feeding according to the corporate standards;

2. weighting the *epimedium* according to the prescription, washing with the water and drying the *epimedium*, processing the reflux extraction three times with the 8-flod (v/w) 70% aqueous solution of the ethanol, the reflux extraction time for once is 3 h, filtrating the extract, combining the filtrate, vacuum recovering the ethanol;

3. concentrating the filtrate to the relative density of 1.10~1.15 (0.07 MPa, 70° C.), spray-drying the filtrate (the inputting temperature is 170° C., the outputting temperature is 70° C.) for obtaining the spray-dried powder, wherein the powder is the ethanol extract of the *epimedium;* d) preparing ethanol extract of the yam:

1. preparing the ingredient: wherein the yam purchased from Jilin Zixin Pharmaceutical Industrial Co., Ltd is in line with the Pharmacopoeia of the People's Republic of China; the quality is strictly controlled before feeding according to the corporate standards;

2. weighting the yam according to the prescription, washing with the water and drying the yam, processing the reflux extraction three times with the 8-flod (v/w) 70% aqueous solution of the ethanol, the reflux extraction time for once is 3 h, filtrating the extract, combining the filtrate, vacuum recovering the ethanol;

3. concentrating the filtrate to the relative density of 1.10~1.15 (0.07 MPa, 70° C.), spray-drying the filtrate (the inputting temperature is 170° C., the outputting temperature is 70° C.) for obtaining the spray-dried powder, wherein the powder is the ethanol extract of the yam;

e) preparing ethanol extract of the *polygonatum:*

1. preparing the ingredient: wherein the *polygonatum* purchased from Jilin Zixin Pharmaceutical Industrial Co., Ltd is in line with the Pharmacopoeia of the People's Republic of China; the quality is strictly controlled before feeding according to the corporate standards;

2. weighting the *polygonatum* according to the prescription, washing with the water and drying the *polygonatum*, processing the reflux extraction three times with the 10-flod (v/w) 70% aqueous solution of the ethanol, the reflux extraction time for once is 3 h, filtrating the extract, combining the filtrate, vacuum recovering the ethanol;

3. concentrating the filtrate to the relative density of 1.10~1.15 (0.07 MPa, 70° C.), spray-drying the filtrate (the inputting temperature is 170° C., the outputting temperature is 70° C.) for obtaining the spray-dried powder, wherein the powder is the ethanol extract of the *polygonatum;* f) preparing ethanol extract of the dodder:

1. preparing the ingredient: wherein the dodder purchased from Jilin Zixin Pharmaceutical Industrial Co., Ltd is in line with the Pharmacopoeia of the People's Republic of China; the quality is strictly controlled before feeding according to the corporate standards;

2. weighting the dodder according to the prescription, washing with the water and drying the dodder, processing the reflux extraction three times with the 8-flod (v/w) 70% aqueous solution of the ethanol, the reflux extraction time for once is 3 h, filtrating the extract, combining the filtrate, vacuum recovering the ethanol;

3. concentrating the filtrate to the relative density of 1.10~1.15 (0.07 MPa, 70° C.), spray-drying the filtrate (the inputting temperature is 170° C., the outputting temperature is 70° C.) for obtaining the spray-dried powder, wherein the powder is the ethanol extract of the dodder;

g) preparing aqueous extract of the wolfberry:

1. preparing the ingredient: wherein the wolfberry purchased from Jilin Zixin Pharmaceutical Industrial Co., Ltd is in line with the Pharmacopoeia of the People's Republic of China; the quality is strictly controlled before feeding according to the corporate standards;

2. weighting the wolfberry according to the prescription, washing with the water and drying the wolfberry, processing the reflux extraction twice with 30-flod pure water at 80° C., the reflux extraction time for once is 3 h, filtrating the extract, combining the filtrate, vacuum recovering the ethanol;

3. concentrating the filtrate to the relative density of 1.10~1.15 (0.07 MPa, 70° C.), spray-drying the filtrate (the inputting temperature is 170° C., the outputting temperature is 70° C.) for obtaining the spray-dried powder, wherein the powder is the ethanol extract of the wolfberry;

h) preparing a fermentation conversion solution of fruits and vegetables:

1. selecting the fruits and vegetables materials;

TABLE 1 fruits and vegetables selected

| Ingredient | nutritional content | Ingredient | nutritional content |
| --- | --- | --- | --- |
| konjac | vitamin B1, B2, citric acid, fermentation conversion matter | carrot | vitamin A, carotene, fermentation conversion matter |
| eggplant | vitamin A, B1, B2, C, fermentation conversion matter | tomato | vitamin A, carotene, citric acid, fermentation conversion matter |
| asparagus | vitamin B1, B2, citric acid, fermentation conversion matter | Chinese cabbage | vitamin, mineral substance, fermentation conversion matter |
| spinach | vitamin A, C, calcium, iron, fermentation conversion matter | celery | vitamin, mineral substance, cellulose, fermentation conversion matter |
| bean sprout | vitamin, saponin, amino acid, fermentation conversion matter | bell pepper | vitamin C, mineral substance, fermentation conversion matter |
| broccoli | vitamin B1, B2, citric acid, fermentation conversion matter | lettuce | vitamin A, mineral substance, fermentation conversion matter |
| cabbage | vitamin B1, B2, citric acid, fermentation conversion matter | pear | fructose, mineral substance, fermentation conversion matter |
| turnip | vitamin B1, B2, citric acid, fermentation conversion matter | ginger | vitamin, mineral substance, fermentation conversion matter |
| cucumber | vitamin B1, B2, citric acid, fermentation conversion matter | taro | vitamin B1, B2, C, mineral substance, fermentation conversion matter |
| pea | vitamin B1, B2, citric acid, fermentation conversion matter | bean | vitamin B1, B2, citric acid, carotene, fermentation conversion matter |
| red pepper | vitamin B1, B2, citric acid, fermentation conversion matter | pumpkin | carotene, mineral substance, fermentation conversion matter |
| celery | vitamin B1, B2, citric acid, fermentation conversion matter | lotus root | iron, tannin, fermentation conversion matter |
| scallion | vitamin B1, B2, citric acid, fermentation conversion matter | cherry | mineral substance, fermentation conversion matter |
| garlic | vitamin B1, B2, citric acid, fermentation conversion matter | kiwi | vitamin C, fermentation conversion matter |
| grape | vitamin B1, B2, citric acid, fermentation conversion matter | plum | organic acid, vitamin, fermentation conversion matter |
| grapefruit | vitamin B1, B2, citric acid, fermentation conversion matter | strawberry | vitamin C, mineral substance, ellagic acid, fermentation conversion matter |
| watermelon | vitamin B1, B2, citric acid, fermentation conversion matter | fig | digest fermentation conversion matter, vitamin, mineral substance |
| peach | vitamin B1, B2, citric acid, fermentation conversion matter | kumquat | vitamin B1, B2, C, fermentation conversion matter |
| orange | vitamin B1, B2, C, fermentation conversion matter | citrus | vitamin C, citric acid, fermentation conversion matter |
| blueberry | vitamin B1, B2, citric acid, fermentation conversion matter | Sounthland pear | vitamin B1, B2, C, citric acid, fermentation conversion matter |
| orange | vitamin B1, B2, citric acid, fermentation conversion matter | melon | vitamin B1, B2, citric acid, fermentation conversion matter |
| banana | vitamin B1, B2, citric acid, fermentation conversion matter | cantaloupe | fructose, potassium, vitamin A, fermentation conversion matter |
| lychee | vitamin B1, B2, citric acid, fermentation conversion matter | pawpaw | vitamin B, C, E, citric acid, carotene, fermentation conversion matter |
| bitter gourd | vitamin B1, B2, citric acid, fermentation conversion matter | onion | vitamin B, C, carotene, fermentation conversion matter |
| leek | vitamin B1, B2, citric acid, fermentation conversion matter | mulberry | vitamin B1, B2, citric acid, fermentation conversion matter |
| pomegranate | vitamin B1, B2, citric acid, fermentation conversion matter | sugar beet | betaine, fermentation conversion matter |
| dragon fruit | vitamin B1, B2, citric acid, fermentation conversion matter | lemon | citric acid, fermentation conversion matter |

2. fermenting and converting the fruits and vegetables, comprising steps of:

2-a) selecting and purchasing cultures;

wherein probiotics culture is purchased from Institute of Microbiology Chinese Academy of Sciences, probiotics is respectively *Lactobacillus acidophilus* CGMCC 1.1854, *Bifidobactreium longum* CGMCC 1.2186, *Lactobacillus delbrueckii subsp bulgaricus* CGMCC 1.1480 and *Streptococcus thermophilus* CGMCC 1.2471, the end of all the cultures are preserved as a starter community in sand tubes;

2-b) preparing main seeds;

wherein preparation of the probiotic main seed comparses steps of (the main seed should be reproduced for no more than ten generations, and the main seed in the preparation is reproduced for four generations):

2-b1) respectively taking a ¹/₁₀ sand tube amount of the *Lactobacillus acidophilus* CGMCC 1.1854, the *Bifidobactreium longum* CGMCC 1.2186, the *Lactobacillus del-*

*brueckii* subsp *bulgaricus* CGMCC 1.1480 and the *Streptococcus thermophilus* CGMCC 1.2471 with a sterile stainless steel spoon, freezing and storing the rest, respectively connecting the sand tubes to 50 ml (250 flask) MRS liquid growth medium (the growth medium comprises 10 g/l peptone, 10 g/l beef extract, 5 g/l yeast extract, 20 g/l glucose, 1 g/l Tween-80, 2 g/l $K_2HPO_4$, 1 g/l Tween-80, 5 g/l NaAC, 2 g/l triammonium citrate, 0.2 g/l $MgSO_4$ and 0.05 g/l $MnSO_4$, the growth medium is sterilized at 121° C. for 20 min), growing at 37° C. with a 100 rpm shaker for 16 h;

2-b2) picking a loop of each colony, respectively streaking the colony loop on MRS solid growth medium (the growth medium comprises 10 g/l peptone, 10 g/l beef extract, 5 g/l yeast extract, 20 g/l glucose, 1 g/l Tween-80, 2 g/l $K_2HPO_4$, 1 g/l Tween-80, 5 g/l NaAC, 2 g/l triammonium citrate, 0.2 g/l $MgSO_4$, 0.05 g/l $MnSO_4$ and 1.5% agar, the growth medium is sterilized at 121° C. for 20 min), growing at 37° C. with an incubator for 16 h;

2-b3) picking the best-growing colony form each the loop, respectively connecting the colony to the 50 ml MRS liquid growth medium, growing at 30° C. with the 180 rpm shaker for 16 h;

2-b4) respectively connecting to the 500 ml MRS liquid growth medium, growing at 37° C. with the 100 rpm shaker for 16 h, adding glycerol until the glycerol takes a proportion of 20%, shaking up, respectively dividing into 1 ml and inputting into a freezing tube as the main seed of the probiotic *Lactobacillus acidophilus*, the *Bifidobactreium longum*, the *Lactobacillus delbrueckii* subsp *bulgaricus* or the *Streptococcus thermophilus*, preservating at −40° C.;

3. preparing working seeds:

wherein preparation of probiotic working seed comparses steps of (the working seed should be reproduced for no more than five generations, and the working seed in the preparation is reproduced for four generations):

3-a) respectively taking the main seeds of the *Lactobacillus acidophilus* CGMCC 1.1854, the *Bifidobactreium longum* CGMCC 1.2186, the *Lactobacillus delbrueckii* subsp *bulgaricus* CGMCC 1.1480 and the *Streptococcus thermophilus* CGMCC 1.2471 with a sterile inoculating loop, respectively streaking to the MRS solid growth medium, growing at 37° C. with the incubator for 16 h;

3-b) picking the best-growing colony form each the loop, respectively connecting the colony to the 50 ml MRS liquid growth medium, growing at 37° C. with the 100 rpm shaker for 16 h;

3-c) respectively connecting to the 500 ml MRS liquid growth medium, growing at 37° C. with the 100 rpm shaker for 16 h;

3-d) respectively connecting to the 5000 ml MRS liquid growth medium, growing at 37° C. with the 100 rpm shaker for 16 h, obtaining the bacteria liquid of the probiotic *Lactobacillus acidophilus*, the *Bifidobactreium longum*, the *Lactobacillus delbrueckii* subsp *bulgaricus* and the *Streptococcus thermophilus*; wherein the above bacteria liquid is all fermentation products in a fermentation container;

4. processing the fruits and vegetables:
4-a) weighing the fruits and vegetables;
4-b) washing, draining and weighing;
4-c) crushing into 40~50 meshes size, putting into a fermentation tank;

wherein for the 3-ton fermentation tank (an effective volume=3 tons×0.8=2.4 tons), an actual feeding amount is controlled at 2400 kg; the fruits and vegetables: water is 1:1, feeding 1200 kg the fruits and vegetables, then adding 1200 kg the water;

5. fermenting and converting a rapid enzymic hydrolysate of the fruits and vegetables:

5-a) respectively adding 5000 ml the bacteria liquid of the *Lactobacillus acidophilus* CGMCC 1.1854, the *Bifidobactreium longum* CGMCC 1.2186, the *Lactobacillus delbrueckii* subsp *bulgaricus* CGMCC 1.1480 and the *Streptococcus thermophilus* CGMCC 1.2471, controlling a fermentation temperature at 23° C., stirring for 15 days;

5-b) filtering with 200 meshes size a filter cloth, abandoning pomace, obtaining the filtrate;

5-c) ultrafiltrating with 100,000 molecular weight ultrafiltration membrane (an inputting pressure is 1.3 kg, an outputting pressure is 0.5 kg), obtaining clear liquid, sealing and preserving at 4° C., wherein the clear liquid is the fermentation conversion solution of the fruits and vegetables;

6. testing:

wherein the main products of the fermentation conversion solution of the fruits and vegetables is mainly lactic acid and acetic acid, therefore, an acidity is identified as a characteristic component, the acidity is:

the acidity of the fermentation conversion solution of the fruits and vegetables: referring to an amount of a 0.1N NaOH solution used in milliliter for titrating 100 ml the fermentation conversion solution of fruits and vegetables, wherein 10 ml samples are often used in a test;

a method for testing comprises steps of: taking 10 ml the fermentation conversion solution of the fruits and vegetables, adding 20 ml the water and 0.5 ml 0.5% phenolphthalein indicator, titrating with the 0.1N NaOH until the liquid is reddish and doesn't fade within 30 sec; calculating: the acidity=the amount of the 0.1N NaOH solution used×10;

result: the acidity of the fermentation conversion solution of the fruits and vegetables is 42.

i) preparing composition:

mixing the above extract and the fermentation conversion solution of the fruits and vegetables according to the following formulation:

mixing 25 g the ethanol extract of the ginseng, 50 g the aqueous extract of the wolfberry, 20 g the ethanol extract of the yam, 50 g the ethanol extract of the *astragalus*, 20 g the ethanol extract of the *epimedium*, 30 g the ethanol extract of the *polygonatum*, 20 g the ethanol extract of the dodder and the fermentation conversion solution of the fruits and vegetables; adding the fermentation conversion solution of the fruits and vegetables for making up the volume to 10,000 ml, wherein the mixture is the composition, dividing into 1000 bottles with 10 ml/bottle for future usage.

Method II:

wherein the active ingredients of the ferment composition of ginseng are: 1.2 g the ginseng, 2.5 g the wolfberry, 2.5 g the yam, 2.5 g the *astragalus*, 0.5 g the *epimedium*, 2.5 g the *polygonatum* and 2.5 g the dodder;

a) preparing the ethanol extract of the ginseng:
the extracting method is basically the same as the method in the method I, deference is that the ginseng is reflux-extracted by the 1-flod (v/w) 70% aqueous solution of the ethanol and the reflux extraction time is 2 h for once;

b) preparing the ethanol extract of the *astragalus*:
the extracting method is basically the same as the method in the method I, the deference is that the *astragalus* is reflux-extracted by the 1-flod (v/w) 70% aqueous solution of the ethanol and the reflux extraction time is 2 h for once;

c) preparing the ethanol extract of the *epimedium*:
the extracting method is basically the same as the method in the method I, the deference is that the *epimedium* is reflux-extracted by the 1-flod (v/w) 70% aqueous solution of the ethanol and the reflux extraction time is 2 h for once;

d) preparing the ethanol extract of the yam:

the extracting method is basically the same as the method in the method I, the deference is that the yam is reflux-extracted by the 1-flod (v/w) 70% aqueous solution of the ethanol and the reflux extraction time is 2 h for once;

e) preparing the ethanol extract of the *polygonatum:* the extracting method is basically the same as the method in the method I, the deference is that the *polygonatum* is reflux-extracted by the 1-flod (v/w) 70% aqueous solution of the ethanol and the reflux extraction time is 2 h for once;

f) preparing the ethanol extract of the dodder:

the extracting method is basically the same as the method in the method I, the deference is that the dodder is reflux-extracted by the 1-flod (v/w) 70% aqueous solution of the ethanol and the reflux extraction time is 2 h for once;

g) preparing the aqueous extract of the wolfberry:

the extracting method is basically the same as the method in the method I, the deference is that the wolfberry is heating-extracted by the 1-flod (v/w) 70% pure water, the heating extraction time is 2 h for once and the heating extraction temperature is 80° C.;

h) preparing the fermentation conversion solution of the fruits and vegetables:

the extracting method is basically the same as the method in the method I, the deference is respectively adding 2000 ml the bacteria liquid of the *Lactobacillus acidophilus* CGMCC 1.1854, the *Bifidobactreium longum* CGMCC 1.2186, the *Lactobacillus delbrueckii* subsp *bulgaricus* CGMCC 1.1480 and the *Streptococcus thermophilus* CGMCC 1.2471, adding 1000 kg the fruits and vegetables and adding 1000 kg the water;

wherein the fermentation time is 18° C., the fermentation time is 10 days;

wherein in the preparation of the bacteria liquid of the *Lactobacillus acidophilus*, the *Bifidobactreium longum*, the *Lactobacillus delbrueckii* subsp *bulgaricus* and the *Streptococcus thermophilus*, the fermentation time is 20° C., the fermentation time is 15 h;

wherein the testing method is the same as the method in the method I, the result has no significant difference;

i) preparing the composition:

the preparing method is basically the same as the method in the method I, the deference is mixing 5 g the ethanol extract of the ginseng, 5 g the ethanol extract of the *astragalus*, 5 g the ethanol extract of the *epimedium*, 5 g the ethanol extract of the yam, 5 g the ethanol extract of the *polygonatum*, 5 g the ethanol extract of the dodder, 5 g the aqueous extract of the wolfberry and the fermentation conversion solution of the fruits and vegetables; adding the fermentation conversion solution of the fruits and vegetables for making up the volume to 1 L, wherein the mixture is the composition.

Method III, wherein the active ingredients of the ferment composition of ginseng are: 1.8 g the ginseng, 3.5 g the wolfberry, 3.5 g the yam, 3.5 g the *astragalus*, 1.5 g the *epimedium*, 3.5 g the *polygonatum* and 3.5 g the dodder;

a) preparing the ethanol extract of the ginseng:

the extracting method is basically the same as the method in the method I, deference is that the ginseng is reflux-extracted by the 5-flod (v/w) 70% aqueous solution of the ethanol and the reflux extraction time is 5 h for once;

b) preparing the ethanol extract of the *astragalus:* the extracting method is basically the same as the method in the method I, the deference is that the *astragalus* is reflux-extracted by the 10-flod (v/w) 70% aqueous solution of the ethanol and the reflux extraction time is 5 h for once;

c) preparing the ethanol extract of the *epimedium:* the extracting method is basically the same as the method in the method I, the deference is that the *epimedium* is reflux-extracted by the 10-flod (v/w) 70% aqueous solution of the ethanol and the reflux extraction time is 5 h for once;

d) preparing the ethanol extract of the yam:

the extracting method is basically the same as the method in the method I, the deference is that the yam is reflux-extracted by the 10-flod (v/w) 70% aqueous solution of the ethanol and the reflux extraction time is 5 h for once;

e) preparing the ethanol extract of the *polygonatum:* the extracting method is basically the same as the method in the method I, the deference is that the *polygonatum* is reflux-extracted by the 8-flod (v/w) 70% aqueous solution of the ethanol and the reflux extraction time is 5 h for once;

f) preparing the ethanol extract of the dodder:

the extracting method is basically the same as the method in the method I, the deference is that the dodder is reflux-extracted by the 10-flod (v/w) 70% aqueous solution of the ethanol and the reflux extraction time is 5 h for once;

g) preparing the aqueous extract of the wolfberry:

the extracting method is basically the same as the method in the method I, the deference is that the wolfberry is heating-extracted by the 150-flod (v/w) 70% pure water, the heating extraction time is 5 h for once and the heating extraction temperature is 90° C.;

h) preparing the fermentation conversion solution of the fruits and vegetables:

the extracting method is basically the same as the method in the method I, the deference is respectively adding 8000 ml the bacteria liquid of the *Lactobacillus acidophilus* CGMCC 1.1854, the *Bifidobactreium longum* CGMCC 1.2186, the *Lactobacillus delbrueckii* subsp *bulgaricus* CGMCC 1.1480 and the *Streptococcus thermophilus* CGMCC 1.2471, adding 1500 kg the fruits and vegetables and adding 1500 kg the water;

wherein the fermentation time is 37° C., the fermentation time is 180 days;

wherein in the preparation of the bacteria liquid of the *Lactobacillus acidophilus*, the *Bifidobactreium longum*, the *Lactobacillus delbrueckii* subsp *bulgaricus* and the *Streptococcus thermophilus*, the fermentation time is 41° C., the fermentation time is 36 h;

wherein the testing method is the same as the method in the method I, the result has no significant difference;

i) preparing the composition:

the preparing method is basically the same as the method in the method I, the deference is mixing 50 g the ethanol extract of the ginseng, 100 g the ethanol extract of the *astragalus*, 5 g ethanol extract of the *epimedium*, 50 g the ethanol extract of the yam, 50 g the ethanol extract of the *polygonatum*, 50 g the ethanol extract of the dodder, 100 g aqueous extract of the wolfberry and the fermentation conversion solution of the fruits and vegetables; adding the fermentation conversion solution of the fruits and vegetables for making up the volume to 1 L, wherein the mixture is the composition.

Preferred Embodiment 2

Preparing Oral Liquid of Ginseng Ferment Composition

Conventional production processes of oral liquid are utilized in the present invention: mixing→filtering→instantaneously sterilizing→canning→capping→leak testing→clarity checking→packaging→testing→storing, wherein the processes before the leak testing are provided in 100,000 class clean area. A production process design and equipment conditions are in line with GMP (Good Manufacturing Practice) requirements of China.

Specifically, a production method comprises steps of:

1. mixing the composition in the method I of the preferred embodiment 1 with a sweetener (specifically, the sweetener is white sugar purchased from Changchun Eurasia department store) (w/v), then putting into a make-up tank, mixing for 30 min for shaking up, instantaneously sterilizing by high heat, wherein the product is the oral liquid of ginseng ferment composition;

2. canning the oral liquid: wherein the oral liquid is canned 10 ml per bottle by filling machines, volumes of the canned oral liquid should be detected during canning in such a manner that difference between the volumes is controlled within the range;

3. capping: wherein the bottle is capped by capping machines, the unqualified products are screened out;

4. leak testing: wherein the capped bottles are tested by a vacuum leak detector;

5. inner packaging: wherein cardboard boxes are utilized, and each the box contains 10 bottles;

6. outer packaging: wherein corrugated boxes are utilized;

7. testing: wherein the products are tested according to the corporate standards;

8. storing: wherein the products are stored in warehouses after passing the tests.

Preferred Embodiment 3

Study on Anti-Fatigue Effects of the Oral Liquid of the Ginseng Ferment Composition 1. Experiment Materials and Methods:

1.1. Animals:

192 Kunming male mice weighting 18~22 g, provided by the Experimental Animal Center of Jilin University, clean grade;

1.2. The Experimental Methods:

a 10.0 statistical software is utilized for analyzing variances, significance level a=0.05;

1.2.1. Dosage Selection:

the mice are divided into four batches, each batch has 48 mice, the mice are randomly divided into four groups according to the weight: three test groups of a group low (5 ml/kg), a group medium (10 ml/kg) as well as a group high (20 ml/kg) (the samples are concentrated by 5 times as test compounds for intragastric administration) and a control group (0.9% NaCl), each group has 12 mice; respectively processing intragastric administration experiments with the oral liquid of the ginseng ferment composition by the above dosage;

processing the intragastric administration for the test groups once a day (the dosage are all 20 ml/kg), lasting for 30 days, then respectively testing each immunity parameter of the animal;

processing a weight-bearing swimming test, a glycogen determination, a serum urea determination and a blood lactic acid determination on the four groups of animals;

1.2.2. The Weight-Bearing Swimming Test:

30 min after the last intragastric administration, tying a lead sheet with 5% the weight of the mouse on a tail of the mouse, wherein the mouse swims in a tank with a depth no less than 30 cm at 25° C., a swimming period from a swimming start to a death of the mouse is recorded;

wherein it is illustrated by table 2 that the swimming periods of the mice of the test group with the dosage of 20.00 ml/kg are longer than the swimming periods of the mice of the control group, the difference has statistical meanings (P=0.0001), which means the oral liquid of the ginseng ferment composition can extend the swimming period of the mouse;

TABLE 2 effect of oral liquid of *ginseng* ferment composition on swimming periods of mice

| dosage (ml/kg) | amount of animals | swimming period (min) | P value |
|---|---|---|---|
| control group | 12 | 4.7 ± 0.7 | |
| 5.0 | 12 | 5.8 ± 1.3 | 0.419 |
| 10.0 | 12 | 6.9 ± 4.2 | 0.054 |
| 20.0 | 12 | 8.7 ± 2.1* | 0.0001 |

Note:
comparison between the test groups and the saline control group, *P < 0.001;

1.2.3. The Glycogen Determination:

30 min after the last intragastric administration, immediately taking a liver out of the mouse from a portion with dislocated cervical vertebra, rinsing the liver with saline, drying with filter paper, accurately weighting 100 mg the liver, adding 8 ml trichloroacetic acid and stirring for 1 min for shaking up, separating by a 3000 r/min centrifugal separator for 15 min, taking supernatant and determining a glycogen content by an anthrone method;

wherein it is illustrated by table 3 that the glycogen contents of the mice of the test group are higher than the glycogen contents of the mice of the control group, the difference has statistical meanings (P<0.05), which means the oral liquid of the ginseng ferment composition can increase the glycogen content of the mouse;

TABLE 3 effect of oral liquid of *ginseng* ferment composition on glycogen contents of mice

| dosage (ml/kg) | amount of animals | swimming period (min) | P value |
|---|---|---|---|
| control group | 12 | 1246 ± 469 | |
| 5.0 | 12 | 1217 ± 781 | 0.923 |
| 10.0 | 12 | 1526 ± 669 | 0.314 |
| 20.0 | 12 | 1854 ± 847* | 0.029 |

Note:
comparison between the test groups and the control group, *P < 0.05;

1.2.4. The Serum Urea Determination:

30 min after the last intragastric administration, putting the mice in the tank with the water depth of 30 cm for swimming at 30° C. for 90 min without bearing, pulling eyes out of the mice for collecting about 0.5 ml whole blood; separating by the 2000 r/min centrifugal separator for 15 min after solidified, taking the supernatant and determining a serum urea content;

TABLE 4 effect of oral liquid of *ginseng* ferment composition on serum urea contents of mice

| dosage (ml/kg) | amount of animals | swimming period (min) | P value |
|---|---|---|---|
| control group | 12 | 10.67 ± 1.61 | |
| 5.0 | 12 | 9.73 ± 1.90 | 0.864 |
| 10.0 | 12 | 9.83 ± 0.99 | 0.733 |
| 20.0 | 12 | 8.57 ± 1.35* | 0.022 |

Note:
comparison between the test groups and the saline control group, *P < 0.05;

wherein it is illustrated by table 4 that the serum urea contents of the mice of the test group are lower than the glycogen contents of the mice of the saline control group, the difference has statistical meanings (P<0.05), which means the oral liquid of the ginseng ferment composition can decrease the serum urea content of the mouse during exercise;

1.2.5. The Blood Lactic Acid Determination:

30 min after the last intragastric administration, taking 20 µL the blood from posterior orbital venous plexus of the mouse and putting into 40 µL permeabilisation, then putting the mouse in the tank with the water depth of 30 cm for swimming at 30° C. for 10 min, respectively taking 20 µL the blood from the posterior orbital venous plexus of the mouse and putting into 40 µL the permeabilisation 0 min and 20 min after swimming, determining the blood lactic acid content by a bio-sensing analyzer;

wherein an under area of a blood lactic acid curve=½×(the blood lactic acid content before swimming+the blood lactic acid content 0 min after swimming)×10+½×(the blood lactic acid content 0 min after swimming+the blood lactic acid content 20 min after swimming)×20;

TABLE 5 effect of oral liquid of *ginseng* ferment composition on under area of blood lactic acid curve of mice

| dosage (ml/kg) | amount of animals | blood lactic acid content before swimming (mmol/L) | blood lactic acid content 0 min after swimming (mmol/L) | blood lactic acid content 20 min after swimming (mmol/L) | under area of blood lactic acid curve |
|---|---|---|---|---|---|
| control group | 12 | 2.2 ± 0.5 | 9.5 ± 2.3 | 4.6 ± 2.1 | 201.5 ± 46.5 |
| 5.0 | 12 | 1.8 ± 0.4 | 9.6 ± 3.5 | 4.1 ± 1.6 | 191.1 ± 66.6 |
| 10.0 | 12 | 2.0 ± 0.7 | 8.1 ± 1.7 | 4.7 ± 1.3 | 182.4 ± 32.1 |
| 20.0 | 12 | 2.1 ± 0.5 | 6.3 ± 1.8* | 3.6 ± 1.5 | 145.2 ± 40.6* |

Note:
comparison between the test groups and the saline control group, *P < 0.01;

wherein it is illustrated by table 5 that the blood lactic acid contents of the mice of the test group with the dosage of 20.0 ml/kg are decreased as well as the under area of the blood lactic acid curve, the difference has statistical meanings (P<0.01).

The fatigue is that muscles can not produce desired or expected contracting force; exhaustion is that the muscle or organs are completely unable to maintain motion. An anti-fatigue feature refers to delaying the fatigue and/or accelerating elimination of the fatigue. The fatigue is mainly manifested in depletion of matrix for the exercise, biochemical state changes of the matrix, accumulation of metabolites, dysfunction of adjustment and coordination functions and decrease of exercise capacity. Therefore, in the study, endurance, the glycogen for the exercise as an energy source and the exercise metabolites in the blood such as urea nitrogen and blood lactic acid are selected as fatigue evaluations.

Improvement of the exercise endurance is the most powerful macroeconomic manifestation of the anti-fatigue feature. In the experiment, the endurance of the mice of the group high is significantly increased as well as the swimming period.

During the body exercise, because the muscle is intensely contracted and oxygen supply is limited, the glycogen and glucose in muscle cell fluid is decomposed and releases ATP as a direct power resource for working for synthesizing energy, at the same time, a large amount of the lactic acid is produced. The increase of the lactic acid leads to the increase of concentration of $H^+$ in the muscle, the decrease of pH, and the fatigue. In the experiment, the lactic acid of the mice of the group high is inhibited as well as the fatigue.

The serum urea nitrogen content of the body increases with the increase of labor and exercise load, and the worse a load adapting ability of the body is, the more significantly the serum urea nitrogen increases; at the same time, the body during the intense exercise drains the glycogen and muscle glycogen, and leads to inhibition of gluconeogenesis feature, the decrease of blood glucose levels, interference of a central nervous system and the fatigue. In the experiment, the serum urea nitrogen contents of the mice of the group high are decreased and the glycogen is increased.

Referring to the above results, the oral liquid of the ginseng ferment composition can improve the endurance, inhibit the fatigue during the exercise.

Detecting the composition obtained in the method II and method III with the same methods, the results have no significant difference from the results of the composition obtained in the method I.

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A method for preparing a pharmaceutical composition for relieving fatigue, comprising:
    mixing the following eight substances for obtaining a mixture, wherein the mixture is the pharmaceutical composition for relieving the fatigue, wherein the eight substances comprise:
    A. ethanol extract of ginseng; B. ethanol extract of *astragalus*; C. ethanol extract of *epimedium*; D. ethanol extract of yam; E. ethanol extract of *polygonatum*; F. ethanol extract of dodder; G. aqueous extract of wolfberry; H. a fermentation conversion solution of fruits and vegetables;
    wherein a method for preparing the A substance comprises:
    processing reflux extraction on the ginseng with an aqueous solution of ethanol for obtaining the extract, wherein the extract is the ethanol extract of the ginseng;

wherein a method for preparing the B substance comprises: processing the reflux extraction on the *astragalus* with the aqueous solution of the ethanol for obtaining the extract, wherein the extract is the ethanol extract of the *astragalus*;

wherein a method for preparing the C substance comprises: processing the reflux extraction on the *epimedium* with the aqueous solution of the ethanol for obtaining the extract, wherein the extract is the ethanol extract of the *epimedium*;

wherein a method for preparing the D substance comprises: processing the reflux extraction on the yam with the aqueous solution of the ethanol for obtaining the extract, wherein the extract is the ethanol extract of the yam;

wherein a method for preparing the E substance comprises: processing the reflux extraction on the *polygonatum* with the aqueous solution of the ethanol for obtaining the extract, wherein the extract is the ethanol extract of the *polygonatum*;

wherein a method for preparing the F substance comprises: processing the reflux extraction on the dodder with the aqueous solution of the ethanol for obtaining the extract, wherein the extract is the ethanol extract of the dodder;

wherein a method for preparing the G substance comprises: processing heating extraction on the wolfberry with pure water for obtaining the extract, wherein the extract is the aqueous extract of the wolfberry;

wherein a method for preparing the H substance comprises steps of: mixing the fruits and the vegetables, a bacteria liquid of *Lactobacillus acidophilus*, a bacteria liquid of the *Bifidobacterium longum*, a bacteria liquid of the *Lactobacillus delbrueckii* subsp *bulgaricus* and a bacteria liquid of the *Streptococcus thermophilus*, fermenting for obtaining a fermentation product, wherein the fermentation product is the fermentation conversion solution of the fruits and vegetables.

2. The method, as recited in claim 1, wherein:
a mass ratio of the ginseng, the wolfberry, the yam, the *astragalus*, the *epimedium*, the *polygonatum* and the dodder is (1.2~1.8):(2.5~3.5):(2.5~3.5):(2.5~3.5):(0.5~1.5):(2.5~3.5):(2.5~3.5).

3. The method, as recited in claim 2, wherein:
a mass ratio of the ginseng, the wolfberry, the yam, the *astragalus*, the *epimedium*, the *polygonatum* and the dodder is (1.2, 1.4 or 1.8):(2.5, 3.0 or 3.5):(2.5, 3.0 or 3.5):(2.5, 3.0 or 3.5):(0.5, 1.0 or 1.5):(2.5, 3.0 or 3.5):(2.5, 3.0 or 3.5).

4. The method, as recited in claim 1, wherein:
in the methods for preparing the A, B, C, D, E and F substances:
the reflux extraction time is 2 h~5 h;
the concentration of the aqueous solution of ethanol is 70% v/v;
wherein in the method for preparing the G substance:
the heating extraction time is 2 h~5 h, the heating extraction temperature is 70° C.~90° C.;
wherein in the method for preparing the H substance:
fermentation temperature is 18° C.~37° C., fermentation time is 10 days to 180 days, a fermentation method is stirring while fermenting.

5. The method, as recited in claim 4, wherein:
in the methods for preparing the A, B, C, D, E and F substances:
the reflux extraction time is 2 h, 3 h or 5 h;
the concentration of the aqueous solution of ethanol is 70% v/v;

the ratio of the aqueous solution of the ethanol and the yam is (1, 8 or 10) ml:1 g;
in the method for preparing the E substance:
the ratio of the aqueous solution of the ethanol and the *polygonatum* is (1, 8 or 10) ml:1 g;
in the method for preparing the F substance:
the ratio of the aqueous solution of the ethanol and the dodder is (1, 8 or 10) ml:1 g;
in the method for preparing the G substance:
the ratio of the pure water of the ethanol and the wolfberry is (1, 30 or 150) ml:1 g;
in the method for preparing the H substance:
the ratio of the bacteria liquid of the *Lactobacillus acidophilus*, the bacteria liquid of the *Bifidobacterium longum*, the bacteria liquid of the *Lactobacillus delbrueckii* subsp *bulgaricus*, the bacteria liquid of the *Streptococcus thermophilus*, the fermentation conversion solution of the fruits and vegetables and the water is (2000, 5000 or 8000) ml:(2000, 5000 or 8000) ml:(2000, 5000 or 8000) ml:(2000, 5000 or 8000) ml:(1000, 1200 or 1500) kg:(1000, 1200 or 1500) kg.

6. The method, as claimed in claim 1, wherein:
the method for preparing the A substance further comprises steps of:
removing the ethanol from the extract, and then concentrating and drying for obtaining a dried product, wherein the dried product is the ethanol extract of the ginseng;
the method for preparing the B substance further comprises steps of:
removing the ethanol from the extract, and then concentrating and drying for obtaining the dried product, wherein the dried product is the ethanol extract of the *astragalus*;
the method for preparing the C substance further comprises steps of:
removing the ethanol from the extract, and then concentrating and drying for obtaining the dried product, wherein the dried product is the ethanol extract of the *epimedium*;
the method for preparing the D substance further comprises steps of:
removing the ethanol from the extract, and then concentrating and drying for obtaining the dried product, wherein the dried product is the ethanol extract of the yam;
the method for preparing the E substance further comprises steps of:
removing the ethanol from the extract, and then concentrating and drying for obtaining the dried product, wherein the dried product is the ethanol extract of the *polygonatum*;
the method for preparing the F substance further comprises steps of:
removing the ethanol from the extract, and then concentrating and drying for obtaining the dried product, wherein the dried product is the ethanol extract of the dodder;
the method for preparing the G substance further comprises: concentrating and drying the extract for obtaining the dried product, wherein the dried product is the aqueous extract of the wolfberry;
the method for preparing the H substance further comprises steps for crushing the fruits and vegetables into 40~50 meshes size before the fermentation;
after the fermentation, the method for preparing the H substance further comprises steps of: filtering the fermentation product, collecting filtrate, ultrafiltering, collecting ultrafiltrate, wherein the ultrafiltrate is the fermentation conversion solution of fruits and vegetables.

7. The method, as recited in claim 1, wherein:
the fruits and vegetables are the mixture of the following 54 kinds of fruits and vegetables:
konjac, eggplant, asparagus, spinach, bean sprout, broccoli, cabbage, turnip, cucumber, pea, red pepper, celery, scallion, garlic, grape, grapefruit, watermelon, peach, orange, blueberry, tangerine, banana, lychee, bitter gourd, leek, pomegranate, dragon fruit, carrot, tomato, Chinese cabbage, celery, bell pepper, lettuce, pear, ginger, taro, bean, pumpkin, lotus root, cherry, kiwi, plum, strawberry, fig, kumquat, citrus, Southland pear, melon, cantaloupe, pawpaw, onion, mulberry, sugar beet and lemon;
wherein, each fruit or vegetable is of the same weight.

8. The method, as claimed in claim 1, wherein:
in the method, 1 L the mixture is prepared by: mixing (5~50) g the ethanol extract of the ginseng, (5~100) g the ethanol extract of the *astragalus*, (5~50) g the ethanol extract of the *epimedium*, (5~50) g the ethanol extract of the yam, (5~50) g the ethanol extract of the *polygonatum*, (5~50) g the ethanol extract of the dodder, (5~100) g the aqueous extract of the wolfberry and the fermentation conversion solution of the fruits and vegetables, adding the fermentation conversion solution of the fruits and vegetables for making up a volume to 1 L;
in the method for preparing the A substance:
a ratio of the aqueous solution of the ethanol and the ginseng is (1~10) ml:1 g;
in the method for preparing the B substance:
the ratio of the aqueous solution of the ethanol and the *astragalus* is (1~10) ml:1 g;
in the method for preparing the C substance:
the ratio of the aqueous solution of the ethanol and the *epimedium* is (1~10) ml:1 g;
in the method for preparing the D substance:
the ratio of the aqueous solution of the ethanol and the yam is (1~10) ml:1 g;
in the method for preparing the E substance:
the ratio of the aqueous solution of the ethanol and the *polygonatum* is (1~10) ml:1 g;
in the method for preparing the F substance:
the ratio of the aqueous solution of the ethanol and the dodder is (1~10) ml:1 g;
in the method for preparing the G substance:
the ratio of the pure water and the wolfberry is (1~150) ml:1 g;
in the method for preparing the H substance:
the ratio of the bacteria liquid of the *Lactobacillus acidophilus*, the bacteria liquid of the *Bifidobacterium longum*, the bacteria liquid of the *Lactobacillus delbrueckii* subsp *bulgaricus*, the bacteria liquid of the *Streptococcus thermophilus*, the fermentation conversion solution of the fruits and vegetables and water is (2000~8000) ml:(2000~8000) ml:(2000~8000) ml:(2000~8000) ml:(1000~1500) kg:(1000~1500) kg.

9. The method, as claimed in claim 8, wherein:
in the method, 1 L the mixture is prepared by: mixing (5, 25 or 50) g the ethanol extract of the ginseng, (5, 50 or 100) g the ethanol extract of the *astragalus*, (5, 20 or 50) g the ethanol extract of the *epimedium*, (5, 20 or 50) g the ethanol extract of the yam, (5, 30 or 50) g the ethanol extract of the *polygonatum*, (5, 20 or 50) g the ethanol extract of the dodder, (5, 50 or 100) g the aqueous extract of the wolfberry and the fermentation conversion solution of the fruits and vegetables, adding the fermentation conversion solution of fruits and vegetables for making up a volume to 1 L;
in the method for preparing the A substance:
a ratio of the aqueous solution of the ethanol and the ginseng is (1, 5 or 10) ml:1 g;
in the method for preparing the B substance:
the ratio of the aqueous solution of the ethanol and the *astragalus* is (1, 6 or 10) ml:1 g;
in the method for preparing the C substance:
the ratio of the aqueous solution of the ethanol and the *epimedium* is (1, 8 or 10) ml:1 g;
in the method for preparing the D substance:
comprises: fermenting and growing *Lactobacillus acidophilus* for obtaining the fermentation production, wherein the fermentation production is the bacteria liquid of the *Lactobacillus acidophilus*; wherein the fermentation temperature is 20° C.~41° C., the fermentation time is 15 h~36 h;
a method for preparing the bacteria liquid of the *Bifidobacterium longum* comprises: fermenting and growing *Bifidobacterium longum* for obtaining the fermentation production, wherein the fermentation production is the bacteria liquid of the *Bifidobacterium longum*; wherein the fermentation temperature is 20° C.~41° C., the fermentation time is 15 h~36 h;
a method for preparing the bacteria liquid of the *Lactobacillus delbrueckii* subsp *bulgaricus* comprises: fermenting and growing *Lactobacillus delbrueckii* subsp *bulgaricus* for obtaining the fermentation production, wherein the fermentation production is the bacteria liquid of the *Lactobacillus delbrueckii* subsp *bulgaricus*; wherein the fermentation temperature is 20° C.~41° C., the fermentation time is 15 h~36 h;
a method for preparing the bacteria liquid of the *Streptococcus thermophilus* comprises: fermenting and growing *Streptococcus thermophilus* for obtaining the fermentation production, wherein the fermentation production is the bacteria liquid of the *Streptococcus thermophilus*; wherein the fermentation temperature is 20° C.~41° C., the fermentation time is 15 h~36 h.

10. The method, as recited in claim 8, wherein:
a method for preparing the bacteria liquid of the *Lactobacillus acidophilus* comprises: fermenting and growing *Lactobacillus acidophilus* for obtaining the fermentation production, wherein the fermentation production is the bacteria liquid of the *Lactobacillus acidophilus*; wherein the fermentation temperature is 20° C.~41° C., the fermentation time is 15 h~36 h;
a method for preparing the bacteria liquid of the *Bifidobacterium longum* comprises: fermenting and growing *Bifidobacterium longum* for obtaining the fermentation production, wherein the fermentation production is the bacteria liquid of the *Bifidobacterium longum*; wherein the fermentation temperature is 20° C.~41° C., the fermentation time is 15 h~36 h;
a method for preparing the bacteria liquid of the *Lactobacillus delbrueckii* subsp *bulgaricus* comprises: fermenting and growing *Lactobacillus delbrueckii* subsp *bulgaricus* for obtaining the fermentation production, wherein the fermentation production is the bacteria liquid of the *Lactobacillus delbrueckii* subsp *bulgaricus*; wherein the fermentation temperature is 20° C.~41° C., the fermentation time is 15 h~36 h;
a method for preparing the bacteria liquid of the *Streptococcus thermophilus* comprises: fermenting and growing *Streptococcus thermophilus* for obtaining the fermentation production, wherein the fermentation production is the bacteria liquid of the *Streptococcus thermophilus*; wherein the fermentation temperature is 20° C.~41° C., the fermentation time is 15 h~36 h.

11. The method, as recited in claim 10, wherein:
a method for preparing the bacteria liquid of the *Lactobacillus acidophilus* comprises: fermenting and growing *Lactobacillus acidophilus* for obtaining the fermentation production, wherein the fermentation production is the bacteria liquid of the *Lactobacillus acidophilus*; wherein the fermentation temperature is 20° C., 37° C. or 41° C., the fermentation time is 15 h, 16 h or 36 h;
a method for preparing the bacteria liquid of the *Bifidobacterium longum* comprises: fermenting and growing *Bifidobacterium longum* for obtaining the fermentation production, wherein the fermentation production is the bacteria liquid of the *Bifidobacterium longum*; wherein the fermentation temperature is 20° C., 37° C. or 41° C., the fermentation time is 15 h, 16 h or 36 h;
a method for preparing the bacteria liquid of the *Lactobacillus delbrueckii* subsp *bulgaricus* comprises: fermenting and growing *Lactobacillus delbrueckii* subsp *bulgaricus* for obtaining the fermentation production, wherein the fermentation production is the bacteria liquid of the *Lactobacillus delbrueckii* subsp *bulgaricus*; wherein the fermentation temperature is 20° C., 37° C. or 41° C., the fermentation time is 15 h, 16 h or 36 h;
a method for preparing the bacteria liquid of the *Streptococcus thermophilus* comprises: fermenting and growing *Streptococcus thermophilus* for obtaining the fermentation production, wherein the fermentation production is the bacteria liquid of the *Streptococcus thermophilus*; wherein the fermentation temperature is 20° C., 37° C. or 41° C., the fermentation time is 15 h, 16 h or 36 h.

12. The method, as recited in claim 10, wherein:
the *Lactobacillus acidophilus* is the *Lactobacillus acidophilus* CGMCC (China General Microbiological Culture Collection) 1.1854, the *Bifidobacterium longum* is the *Bifidobacterium longum* CGMCC 1.2186, the *Lactobacillus delbrueckii* subsp *bulgaricus* is the *Lactobacillus delbrueckii* subsp *bulgaricus* CGMCC 1.1480, the *Streptococcus thermophilus* is the *Streptococcus thermophilus* CGMCC 1.2471.

13. The method, as recited in claim 11, wherein:
the *Lactobacillus acidophilus* is the *Lactobacillus acidophilus* CGMCC (China General Microbiological Culture Collection) 1.1854, the *Bifidobacterium longum* is the *Bifidobacterium longum* CGMCC 1.2186, the *Lactobacillus delbrueckii* subsp *bulgaricus* is the *Lactobacillus delbrueckii* subsp *bulgaricus* CGMCC 1.1480, the *Streptococcus thermophilus* is the *Streptococcus thermophilus* CGMCC 1.2471.

14. A pharmaceutical composition for relieving fatigue prepared by the method recited in claim 13.

15. The method, as recited in claim 1, wherein:
a method for preparing the bacteria liquid of the *Lactobacillus acidophilus*
wherein in the method for preparing the G substance:
the heating extraction time is 2 h, 3 h or 5 h, the heating extraction temperature is 70° C., 80° C. or 90° C.;
wherein in the method for preparing the H substance:
fermentation temperature is 18° C., 23° C. or 37° C., fermentation time is 10 days, 15 days or 180 days, a fermentation method is stirring while fermenting.

16. The method, as recited in claim 15, wherein:
the *Lactobacillus acidophilus* is the *Lactobacillus acidophilus* CGMCC (China General Microbiological Culture Collection) 1.1854, the *Bifidobacterium longum* is the *Bifidobacterium longum* CGMCC 1.2186, the *Lactobacillus delbrueckii* subsp *bulgaricus* is the *Lactobacillus delbrueckii* subsp *bulgaricus* CGMCC 1.1480, the *Streptococcus thermophilus* is the *Streptococcus thermophilus* CGMCC 1.2471.

17. The method, as recited in claim 1, wherein:
the *Lactobacillus acidophilus* is the *Lactobacillus acidophilus* CGMCC (China General Microbiological Culture Collection) 1.1854, the *Bifidobacterium longum* is the *Bifidobacterium longum* CGMCC 1.2186, the *Lactobacillus delbrueckii* subsp *bulgaricus* is the *Lactobacillus delbrueckii* subsp *bulgaricus* CGMCC 1.1480, the *Streptococcus thermophilus* is the *Streptococcus thermophilus* CGMCC 1.2471.

18. A pharmaceutical composition for relieving fatigue prepared by the method recited in claim 1.

* * * * *